US008236990B2

(12) United States Patent
Smith et al.

(10) Patent No.: US 8,236,990 B2
(45) Date of Patent: Aug. 7, 2012

(54) TRIARYLAMINE COMPOUNDS, COMPOSITIONS AND USES THEREFOR

(75) Inventors: Eric Maurice Smith, Hockessin, DE (US); Nora Sabina Radu, Landenberg, PA (US); Norman Herron, Newark, DE (US); Arthur Dabrowski, Herts (GB); Frederick P. Gentry, Bear, DE (US); Gene M. Rossi, Wilmington, DE (US); Gary A. Johansson, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/419,810

(22) Filed: Apr. 7, 2009

(65) Prior Publication Data

US 2009/0200933 A1 Aug. 13, 2009

(51) Int. Cl.
*C07C 211/55* (2006.01)
*C08G 61/12* (2006.01)
*C09K 19/38* (2006.01)

(52) U.S. Cl. ......... 564/330; 528/397; 528/401; 428/1.4; 428/1.6

(58) Field of Classification Search ........................ None
See application file for complete search history.

(56) References Cited

U.S. PATENT DOCUMENTS 3,265,498 A 8/1966 Lutes
3,955,978 A 5/1976 Rochlitz
4,047,948 A 9/1977 Horgan
4,047,949 A 9/1977 Horgan
4,086,209 A 4/1978 Hara et al.
4,115,116 A 9/1978 Stolka et al.
4,233,384 A 11/1980 Turner et al.
4,265,990 A 5/1981 Stolka et al.
4,299,897 A 11/1981 Stolka et al.
4,322,487 A 3/1982 Merrill et al.
4,346,158 A 8/1982 Pai et al.
4,504,564 A 3/1985 Pai et al.
4,517,354 A 5/1985 D'Alelio
4,665,000 A * 5/1987 Tokoli et al. .................... 430/85
4,714,779 A 12/1987 Turner et al.
4,801,517 A 1/1989 Frechet et al.
4,933,053 A 6/1990 Tieke
4,933,245 A 6/1990 Akasaki et al.
4,937,165 A 6/1990 Ong et al.
4,946,754 A 8/1990 Ong et al.
5,077,142 A 12/1991 Sakon et al.
5,130,481 A 7/1992 Khanna
5,155,200 A 10/1992 Limburg et al.
5,237,045 A 8/1993 Burchill
5,449,564 A 9/1995 Nishio et al.
5,554,450 A 9/1996 Shi et al.
5,652,067 A 7/1997 Ito et al.
5,677,097 A 10/1997 Nukada
5,681,664 A 10/1997 Tamano et al.
5,681,679 A 10/1997 Schank et al.
5,763,110 A 6/1998 Hu et al.
5,789,128 A 8/1998 Adachi et al.
5,792,557 A 8/1998 Nakaya et al.
5,846,681 A 12/1998 Yu
5,882,829 A 3/1999 Hsieh et al.
5,891,587 A 4/1999 Hu et al.
5,929,194 A 7/1999 Woo et al.
5,962,631 A 10/1999 Woo et al.
5,994,573 A 11/1999 Tachikawa
6,020,426 A 2/2000 Yamaguchi et al.
6,107,439 A 8/2000 Yanus et al.
6,107,452 A 8/2000 Miller et al.
6,132,913 A 10/2000 Fuller et al.
6,143,452 A 11/2000 Sakimura et al.
6,150,426 A 11/2000 Curtin et al.
6,303,238 B1 10/2001 Thompson et al.
6,361,885 B1 3/2002 Chou
6,376,106 B1 4/2002 Uchida et al.
6,376,694 B1 4/2002 Uchida et al.
6,376,695 B1 4/2002 Kushibiki et al.
6,517,957 B1 2/2003 Senoo et al.
6,558,818 B1 5/2003 Samuel et al.
6,646,164 B2 11/2003 Uemura et al.
6,689,491 B1 2/2004 Nii
2001/0017155 A1 8/2001 Bellmann et al.
2001/0019782 A1 9/2001 Igarashi et al.
2002/0050597 A1 5/2002 Hirose et al.
2002/0055014 A1 5/2002 Okada et al.
2002/0057050 A1 5/2002 Shi
2003/0064308 A1 4/2003 Kita
2003/0099862 A1 5/2003 O'Neill et al.
2003/0162053 A1 8/2003 Marks et al.
2003/0207152 A1 11/2003 Hsieh et al.
2003/0224205 A1 12/2003 Li et al.
2003/0225234 A1 12/2003 Jaycox et al.
2003/0232264 A1 12/2003 Tokarski et al.
2004/0004433 A1 1/2004 Lamansky et al.
2004/0102577 A1 5/2004 Hsu et al.
2005/0067951 A1 3/2005 Richter et al.
2005/0089780 A1 4/2005 Jubran et al.
2005/0227465 A1 10/2005 Smith et al.

FOREIGN PATENT DOCUMENTS

DE 19643097 A1 4/1998

(Continued)

OTHER PUBLICATIONS

Database CAPLUS on STN, Acc. No. 1987:11164, JP 61098353 (May 16, 1986) (abstract).*

(Continued)

*Primary Examiner* — Brian J Davis

(57) ABSTRACT

The present invention relates to triarylamine compounds, compositions comprising such compounds, and electronic devices and applications comprising at least one layer containing at least one of the new compounds. The compounds can be used as monomers to create homopolymers or copolymers.

7 Claims, 1 Drawing Sheet

FOREIGN PATENT DOCUMENTS

| | | | |
|---|---|---|---|
| DE | 10109463 | A1 | 10/2002 |
| EP | 0372979 | A2 | 6/1990 |
| EP | 848579 | A | 6/1998 |
| EP | 650955 | A1 | 8/1998 |
| EP | 866110 | A | 9/1998 |
| EP | 1154331 | A1 | 11/2001 |
| EP | 1191612 | A1 | 3/2002 |
| EP | 1464691 | A2 | 10/2004 |
| EP | 1284258 | A2 | 2/2006 |
| EP | 1191614 | B1 | 6/2009 |
| FR | 02623638 | A1 | 5/1989 |
| JP | 51093224 | A | 8/1976 |
| JP | 61098353 | A | 5/1986 |
| JP | 61228450 | A | 10/1986 |
| JP | 02190864 | A | 7/1990 |
| JP | 03102361 | A | 4/1991 |
| JP | 03158862 | A | 7/1991 |
| JP | 03203739 | A | 9/1991 |
| JP | 03208057 | A | 9/1991 |
| JP | 03264592 | A | 11/1991 |
| JP | 03290665 | A | 12/1991 |
| JP | 04021688 | A | 1/1992 |
| JP | 04182656 | A | 6/1992 |
| JP | 04300854 | A | 10/1992 |
| JP | 04330079 | A | 11/1992 |
| JP | 04338967 | A | 11/1992 |
| JP | 05032596 | A | 2/1993 |
| JP | 05112509 | A | 5/1993 |
| JP | 05150476 | A | 6/1993 |
| JP | 05165239 | A | 7/1993 |
| JP | 05234678 | A | 9/1993 |
| JP | 05239454 | A | 9/1993 |
| JP | 05247459 | A | 9/1993 |
| JP | 05249706 | A | 9/1993 |
| JP | 05249716 | A | 9/1993 |
| JP | 06065569 | A | 3/1994 |
| JP | 06107605 | A | 4/1994 |
| JP | 06120538 | A | 4/1994 |
| JP | 06130701 | A | 5/1994 |
| JP | 06234709 | A | 8/1994 |
| JP | 07072634 | A | 3/1995 |
| JP | 07089229 | A | 4/1995 |
| JP | 08095270 | A | 4/1996 |
| JP | 08099941 | A | 4/1996 |
| JP | 08146629 | A | 6/1996 |
| JP | 08179526 | A | 7/1996 |
| JP | 08292586 | A | 11/1996 |
| JP | 08314169 | A | 11/1996 |
| JP | 09268284 | A | 10/1997 |
| JP | 10078669 | A | 3/1998 |
| JP | 10092578 | A | 4/1998 |
| JP | 10104859 | A | 4/1998 |
| JP | 10106750 | A | 4/1998 |
| JP | 10233287 | A | 9/1998 |
| JP | 10251633 | A | 9/1998 |
| JP | 10265773 | A | 10/1998 |
| JP | 11060718 | A | 3/1999 |
| JP | 2000056490 | A | 2/2000 |
| JP | 2000063337 | A | 2/2000 |
| JP | 2000105475 | A | 4/2000 |
| JP | 2000143786 | A | 5/2000 |
| JP | 2000297068 | A | 10/2000 |
| JP | 2001060010 | A | 3/2001 |
| JP | 2001089428 | A | 4/2001 |
| JP | 2001172284 | A | 6/2001 |
| JP | 2001279237 | A | 10/2001 |
| JP | 2002080570 | A | 3/2002 |
| JP | 2002167365 | A | 6/2002 |
| JP | 2002179630 | A | 6/2002 |
| JP | 2002212150 | A | 7/2002 |
| JP | 2002235077 | A | 8/2002 |
| JP | 2003142269 | A | 5/2003 |
| JP | 2003213002 | A | 7/2003 |
| JP | 2003257676 | A | 9/2003 |
| JP | 2003297582 | A | 10/2003 |
| JP | 2004030942 | A | 1/2004 |
| JP | 2004067970 | A | 3/2004 |
| JP | 2004093794 | A | 3/2004 |
| JP | 2004176024 | A | 6/2004 |
| JP | 2004184569 | A | 7/2004 |
| JP | 2005060387 | A | 3/2005 |
| JP | 2005085599 | A | 3/2005 |
| JP | 2005108804 | A | 4/2005 |
| JP | 2005516059 | T | 6/2005 |
| JP | 2005220088 | A | 8/2005 |
| JP | 2005221539 | A | 8/2005 |
| JP | 2005259442 | A | 9/2005 |
| JP | 2005284268 | A | 10/2005 |
| JP | 2007525498 | T | 9/2007 |
| JP | 2007527420 | T | 9/2007 |
| WO | 00/53565 | A1 | 9/2000 |
| WO | 00/70655 | A2 | 11/2000 |
| WO | 01/41512 | A1 | 6/2001 |
| WO | 0149769 | A1 | 7/2001 |
| WO | 02/02714 | A2 | 1/2002 |
| WO | 02/15645 | A1 | 1/2002 |
| WO | 0201653 | A2 | 1/2002 |
| WO | 03/064373 | A | 8/2003 |
| WO | 2004005406 | A2 | 1/2004 |

OTHER PUBLICATIONS

Database CAPLUS on STN, Acc. No. 1993:29979, Karasawa et al., JP 0422563 (Aug. 14, 1992) (abstract).

International Searching Authority, Written Opinion, PCT/US2005/010852, which is the PCT counterpart of the currently pending U.S. Appl. No. 11/093,455, Sep. 30, 2006.

Database CAPLUS on STN, Acc. No. 1987:11164, JP 61098353 A (May 16, 1986) (abstract).

M. Thelakkat et al., Synthesis and Properties of New Hole Transport Materials for Organic Light Emitting Devices, Proceedings of the SPIE—Conference on Organic Light-Emitting Materials and Devices, vol. 3148:306-312, 1997, XP002341801.

C. Jaeger et al., Novel Hole Transporting Poly(Triphenyldiamine)s for Application in Hybrid Solar Cells, Proceedings of the SPIE—Organic Photovoltaics, vol. 4108:104-111, 2001, XP001191043.

G. F. Mielke et al., Fluorenylidene-Linked Triarylamines As New Hole-Transporting Materials for Organic Light-Emitting Diodes (OLEDS), Polymer Preprints, vol. 4191):877-878, 2000, XP001012460.

Patent Abstracts of Japan, vol. 2002(02), Apr. 2, 2002 & JP 2001 279237 A, Fuji Photofilm Co. Ltd., Oct. 10, 2001, Abstract p. 8.

Patent Abstracts of Japan, vol. 1999(01), Jan. 29, 1999, & JP 10 265773 A, Toyo Ink MFG Co., Ltd., Oct. 6, 1998, Abstract, p. 8-9.

Patent Abstracts of Japan, vol. 2000(05), Sep. 14, 2000 & JP 2000 056490 A, Canon Inc., Feb. 25, 2000, Abstract, p. 8.

Patent Abstracts of Japan, vol. 2003(12), Dec. 5, 2003 & JP 2004 093794 A, Canon Inc., Mar. 25, 2004, Abstract, p. 9.

Atent Abstracts of Japan, vol. 2003(12), Dec. 5, 2003 & JP 2004 184569 A, Canon Inc., Jul. 2, 2004, Abstract, p. 10.

G. Gustafsson et al., Flexible light-emitting diodes made from soluble cnoducting polymers, Nature, 357:477-479, Jun. 11, 1992.

John F. Hartwig, Palladium-Catalyzed Amination of Aryl Halides and Sulfonates, Modern Arene Chemistry, Astruc, D., Editor, Wiley-VCH Verlag GmbH & Co. KGaA, Weinheim, Germany, pp. 107-168, 2002.

I. Colon et al., High Molecular Weight Aromatic Polymers by Nickel Coupling of Aryl Polychlorides, Journal of Polymer Science: Part A: Polymer Chemistry, vol. 28:367-383, 1990.

John P. Wolfe et al., Simple, Efficient Catalyst System for the Palladium-Catalyzed Amination of Aryl Chlorides, Bromides, and Triflates, J. Org. Chem., vol. 65:1158-1174, 2000.

Joseph P. Sadighi et al., Palladium-Catalyzed Synthesis of Monodisperse, Controlled-Length, and Functionalized Oligoanilines, J. Am. Chem. Soc., vol. 120:4960-4976, May 12, 1998.

Christophe Desmarets et al., Nickel-catalysed sequential amination of aryl- and heteroaryl di- and trichlorides, Tetrahedron, vol. 57:7657-7664, 2001.

Artis Klapars et al., A General and Efficient Copper Catalyst for the Amidation of Aryl Halides and the N-Arylation of Nitrogen Heterocycles, J. Am. Chem. Soc., vol. 123:7727-7729, Jul. 12, 2001.

D. F. O'Brien et al., Electrophosphoresence from a doped polymer light emitting diode, Synthetic Metals, vol. 116:379-383, 2001.
I. H. Campbell et al., Excitation transfer processes in a phosphor-doped poly(p-phenylene vinylene) light-emitting diode, Physical Review B, vol. 65:085210-1-085210-8, 2002.
Bacher, A. et al., Photo-Cross-Linked Triphenylenes as Novel Insoluble Hole Transport Materials in Organic LEDs, Macromolecules, 1999, 4551-4557, 32, American Chemical Society.
Bayerl et al, Crosslinkable hole-transport materials for preparation of multilayer organic light emitting devices by spin-coating, Macromol. Rapid Commun., 20(4), pp. 224-228; 1999.
Braig, T. et al., Crosslinkable hole-transporting polymers by palladium-catalyzed C-N-coupling reaction, Macromol. Rapid Commun., 2000, 583-589, 21(9), Wiley-VCH Verlag GmbH, Weinheim.
Chihaya et al; Durability Characteristics of Aminopyrene Dimer Molecules as an Emitter in Organic Multilayered Electroluminescent Diodes; Japanese Journal of Applied Physics, Part 1: Regular Papers, Short Notes and Review Papers, 1996, 35(9A), pp. 4819-4825.
Ego et al; Triphenylamine-Substituted Polyfluorene—A Stable Blue-Emitter with Improved Charge Injection for Light-Emitting Diodes; Advanced Materials, 2002, 14(11), pp. 809-811.
Holmes et al; The Photo-Ionization of Some Triphenylmethane-Leucocyanides Containing Certain Groups Substituted in the para-Position Dissolved in 1,2-Dichloroethane; Journal of Physical Chemistry, 1958, 62, p. 884.
Markus, John: 'Electronics and Nucleonics Dictionary', Jun. 19 0005, McGraw-Hill, Inc, pp. 470 and 476.
Nuyken, O. et al., Crosslinkable hole- and electron-transport materials for application in organic light emitting devices (OLEDs), Designed Monomers and Polymers, 2002, 195-210, 5(2,3).
Sato et al; Stability of Organic Electroluminescent Diodes; Molecular Crystals and Liquid Crystals Science and Technology, 1994, vol. 252-253, pp. 435-442.
Schmitz et al.; A Combinatorial Study of the Dependence of Organic LED Characteristics on Layer Thickness; Advanced Materials 1999, 11, No. 10 p. 821-826.
Shu et al; Highly Efficient Blue-Light-Emitting Diodes from Polyfluorene Containing Bipolar Pendant Groups; Macromolecules 2003, 36(18), pp. 6698-6703.
Thelakkat et al; Synthesis and Properties of Novel Hole Transport Materials for Electroluminescent Devices, Macromolecular Symposia, vol. 125 (1998), pp. 157-164.
Thelakkat et al; Novel Triarylamine Polymers as Hole Transport Materials in OLEDs; Polymer Preprints, Aug. 1999, 40(2), pp. 1230-1231.
Wolfe, J. et al; Nickel-Catalyzed Amination of Aryl Chlorides; Journal American Chemical Society, vol. 119, 1997, pp. 6054-6058.
International Search Report and Written Opinion for PCT/US2005/05584; M. Kovecs, Authorized Officer; Jun. 30, 2005.
International Search Report for PCT/US2005/05579; M. Kovecs, Authorized Officer; Jun. 3, 2005.
Borsenberger, et al; Effects of the Dipole Moment on Charge Transport in Disordered Molecular Solids. Journal of Physical Chemistry. 1993, vol. 97, pp. 4815-4819.
Bradley et al., "Electrophosphoresence from a Doped Polymer Light Emitting Diode," Synth. Met. vol. 116, No. 1-3, Jan. 20, 2001, pp. 379-383.
Faber et al; Anodic Oxidation of Novel Hole-Transporting Materials Derived from Tetraarylbenzidines. Electrochemical and Spectroscopic Characterization. Collection of Czechoslovak Chemcial Communications, Institute of Organic Chemistry and Biochemistry, Prague. 2000, vol. 65, No. 9, pp. 1403-1418.
Haeussermann; Zur Kenntniss Der Tertiaeren Aromatischen Amine. Chemische Berichte. 1906, vol. 39, pp. 2762-2765 (Non English—No English translation submitted).
Smith et al; Reactions of Triphenylamine and Some Related Compounds with Thionyl Chloride. Journal of Applied Chemistry, 1969, p. 621.
Tolbert et al; The Absorption Spectra of Some N-Phenyl-P,P'-Diaminotriphenylmethane Dyes. Journal of the American Chemical Society, 1945, vol. 67, No. 6, pp. 887-893.
Zhao et al; Design and Synthesis of 1-3 Stable Triarylamines for Hole-Transport Applications. Tetrahedron Letters. 2001. vol. 42, No. 27, pp. 4421-4424.
EESR Jul. 26, 2011; Extended European Search Report for Application No. EP10011539; Jul. 26, 2011.

* cited by examiner

TRIARYLAMINE COMPOUNDS, COMPOSITIONS AND USES THEREFOR

RELATED APPLICATION INFORMATION

This application claims priority under 35 U.S.C. 120 from U.S. patent application Ser. No. 11/093,455, filed Mar. 30, 2005 (incorporated by reference herein), which in turn claimed priority under 35 U.S.C. §119(e) from U.S. Provisional Application No. 60/557,964, filed on Mar. 31, 2004, which is incorporated by reference herein in its entirety.

BACKGROUND OF THE INVENTION

1. Field of the Invention

The present invention relates to triarylamine compounds useful as charge transport materials in electronic devices and other applications.

2. Background

In organic photoactive electronic devices, such as organic light emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

There is a continuing need for charge transport materials for use in electronic devices and other applications.

SUMMARY OF THE INVENTION

One aspect of the invention is a new triarylamine compounds having Formula I or III:

(I)

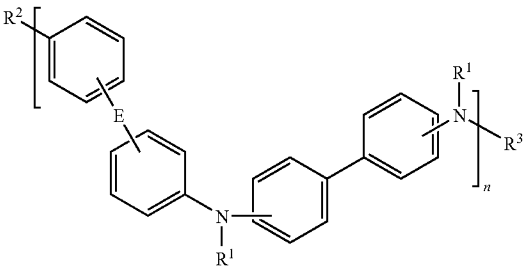

or

-continued (III)

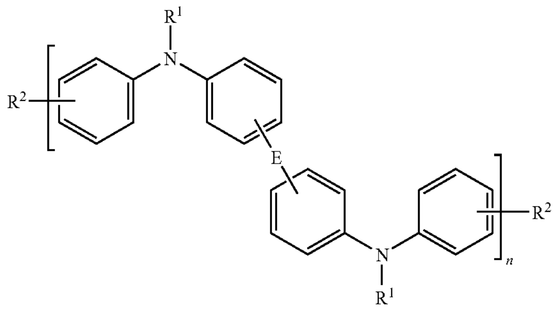

wherein n is an integer of at least 1, $R^1$ is selected from aryl, heteroaryl, fluoroaryl, and fluoroheteroaryl and wherein $R^1$ may be same or different in each occurrence, $R^3$ is selected from H and $R^1$. $R^2$ is selected from H, $R^1$, alkyl, fluoroalkyl, Cl, Br, I and an arylamino group of Formula (II), (II)

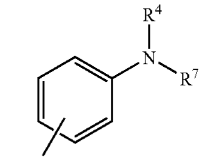

wherein $R^4$ is selected from aryl, H, $R^1$, alkyl, and fluoroalkyl, $R^7$ is selected from aryl, heteroaryl, fluoroaryl, and fluoroheteroaryl, E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$ and n is greater than 1 and m is 1, at least one of $R^5$ and $R^6$ is not hydrogen or a hydrocarbon.

Also provided are polymers and copolymers prepared by polymerizing functional monomers having the Formula (I) or (III) as defined hereinabove.

Other aspects of the present invention include electronic devices and other applications having at least one layer comprising at least one compound described above.

In another aspect of the present invention, compositions comprising at least one of the above compounds are provided. Liquid compositions including at least one compound described herein can be in the form of a solution, dispersion or emulsion.

The foregoing general description and the following detailed description are exemplary and explanatory only and are not restrictive of the invention, as defined in the appended claims.

DESCRIPTION OF THE DRAWINGS

The invention is illustrated by way of example and not limitation in the accompanying figures.

DETAILED DESCRIPTION OF THE EMBODIMENTS

Figure 1:
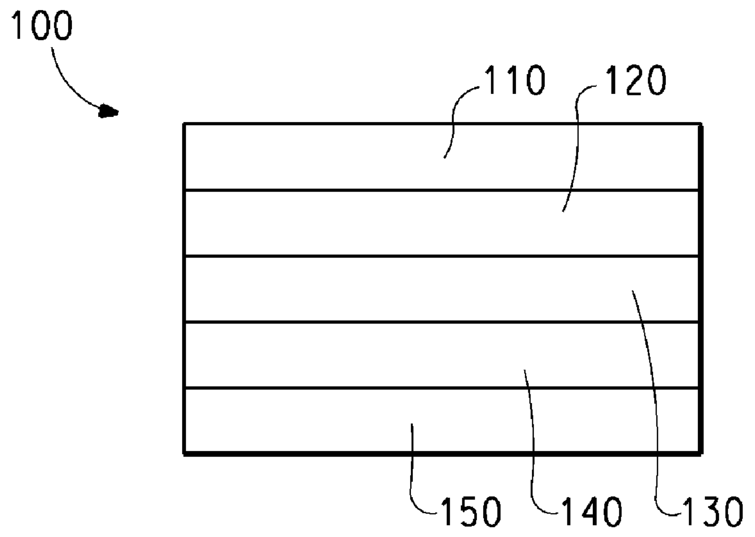
FIG. 1: An illustrative example of one organic electronic device comprising at least one layer comprising at least one of the new compounds disclosed herein.

The present invention provides new compounds, new methods of making said compounds, compositions comprising at least one of the new compounds, electronic devices and other applications comprising at least one layer comprising at least one of the new compounds, and methods for making devices containing the compounds. One aspect of the present are compounds having Formula I or III:

(I)

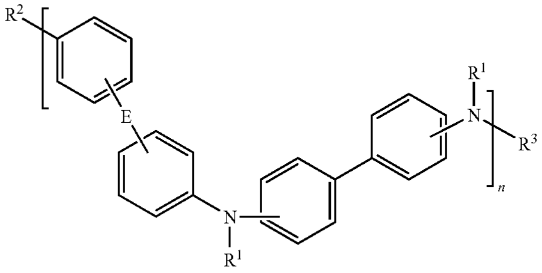

or (III)

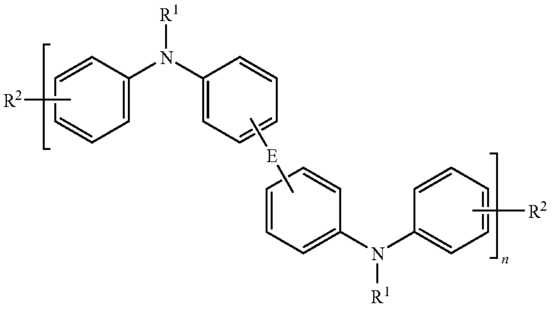

wherein n is an integer of at least 1

$R^1$ is selected from aryl, heteroaryl, fluoroaryl, and fluoroheteroaryl and wherein the $R^1$ may be same or different in each occurrence, $R^3$ is selected from H and $R^1$, $R^2$ is selected from H, $R^1$, alkyl, fluoroalkyl, Cl, Br, I and an arylamino group of formula (II), (II)

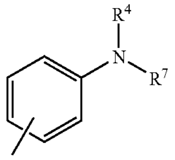

$R^4$ is selected from aryl, H, $R^1$, alkyl, and fluoroalkyl, $R^7$ is selected from aryl, heteroaryl, fluoroaryl, and fluoroheteroaryl, E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (I) and III has one or more substituents independently selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (I) and III can together form an aromatic or non-aromatic ring. In further embodiments, adjacent substituents on a single ring can be linked to form a fused aromatic or non-aromatic ring.

In some embodiments $R^1$ is aryl.

In some embodiments, $R^1$ is selected from phenyl, 1-naphthyl, and 2-naphthyl. In some embodiments, n=1, $R^2$ is H, and $R^3$ is selected from phenyl, 1-naphthyl, and 2-naphthyl.

In some embodiment, $R^1$ is selected from fluoroaryl and fluoroheteroaryl, where the groups can have up to 7 fluorine atoms.

In some embodiments, $R^2$ is H or aryl. In some embodiments, $R^2$ is different from $R^3$. In some embodiments, $R^2$ is H and $R^3$ is aryl.

In some embodiments, $R^4$ is aryl.

In some embodiment, $R^7$ is selected from fluoroaryl and fluoroheteroaryl, where the groups can have up to 7 fluorine atoms.

In one embodiment, the new compounds have Formula IV (IV)

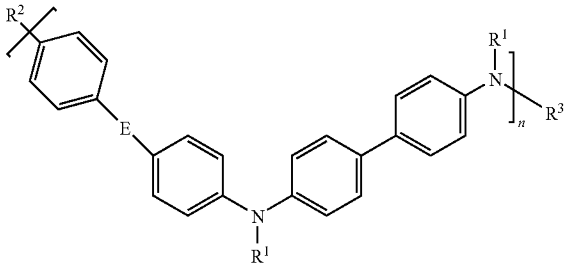

wherein n is an integer of at least 1, $R^1$ is selected from aryl, heteroaryl, fluoroaryl, and fluoroheteroaryl (wherein the fluoroaryl and fluoroheteroaryl is substituted with one or more fluorine atoms and in some embodiments up to 7 fluorine atoms), and $R^1$ may be different at each occurrence. In some embodiments, $R^1$ is aryl. $R^2$ is selected from H, $R^1$, alkyl, fluoroalkyl, arylamino of formula (II), Cl, Br, I. In some embodiments, $R^2$ is H. $R^3$ is selected from H and $R^1$. In some embodiments, $R^3$ is aryl. $R^4$ is selected from aryl, H, $R^1$, alkyl, fluoroalkyl. In some embodiments $R^4$ is aryl. In some embodiments, $R^2$ is different from $R^3$. In some embodiments, $R^2$ is H and $R^3$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, and fluoroaryloxy and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of Formula (IV) has a substituent selected from H, F, alkyl, aryl, alkoxy, aryloxy, fluoroalkyl, fluoroaryl, fluoroalkoxy, and fluoroaryloxy.

In some embodiments, $R^1$ is selected from phenyl, 1-naphthyl, and 2-naphthyl. In some embodiments, n=1, $R^2$ is H, and $R^3$ is selected from phenyl, 1-naphthyl, and 2-naphthyl.

Polymers and copolymers can be prepared by polymerizing multiple functional monomers having the Formulae I, III, and IV, wherein the monomer may be the same or different. As used herein, the term "functional monomer" is intended to mean a compound having at least reactive group, and being capable of reacting with other compounds having the same or different reactive groups.

The practical upper limit of n in Formulae (I), (III) and (IV) is determined in part by the desired solubility of a compound in a particular solvent or class of solvents. As the value of n increases, the molecular weight of the compound increases. The increase in molecular weight is generally expected to result in a reduced solubility of the compound in a particular solvent. Moreover, in one embodiment, the value of n at which a compound becomes substantially insoluble in a given solvent is dependent in part upon the structure of the compound. For example, a compound containing multiple phenyl groups may become substantially insoluble in an organic solvent when n is much less than about $10^4$. As another example, a compound containing fewer phenyl groups and/or phenyl groups with particular functional groups may be soluble in a given solvent even though n is about $10^4$ or greater, even $10^5$ or $10^6$. The selection of the value of n and a solvent is within the purview of one skilled in the art.

Also provided are compounds comprising copolymers prepared by combining multiple functional monomers of the compounds described herein. Such monomers can be grouped into three classes as follows:

Group 1

A1

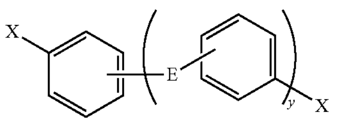

C1

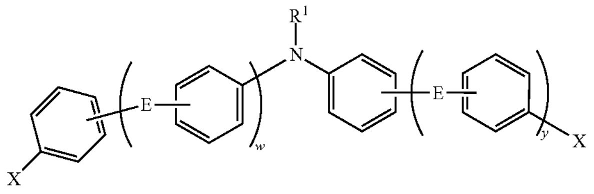

A2

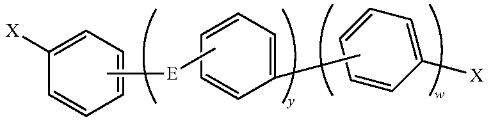

C2

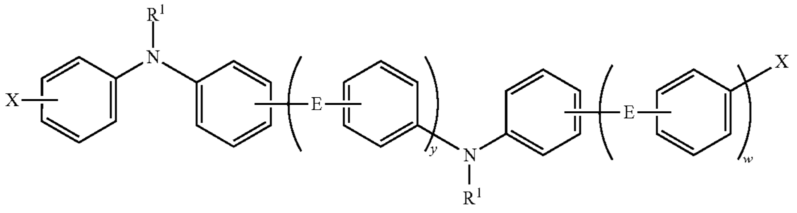

B

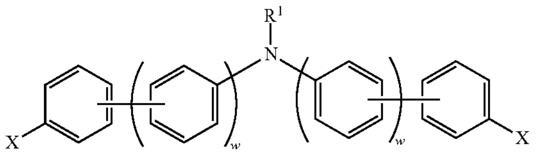

C3

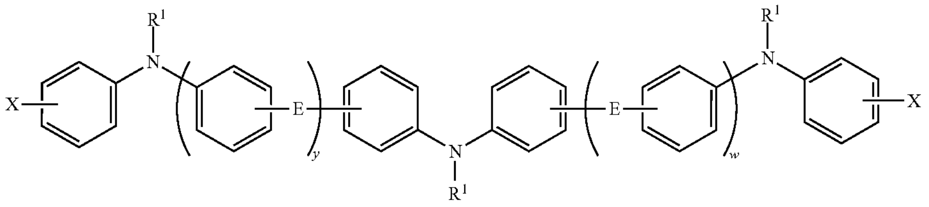

-continued

Group 2

D1

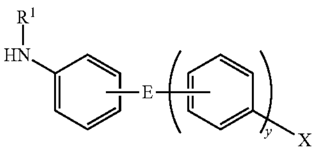

D2

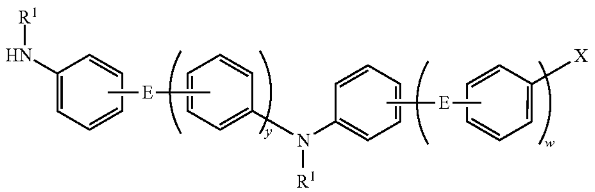

D3

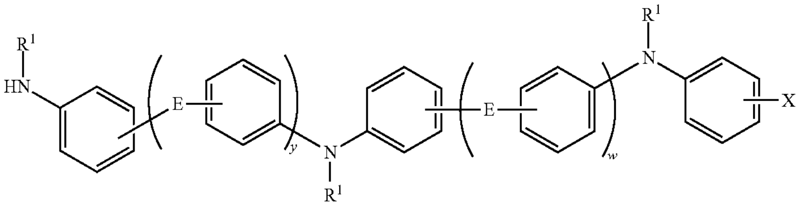

Group 3

A1

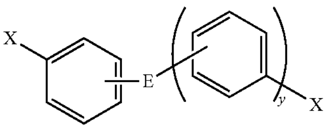

E1

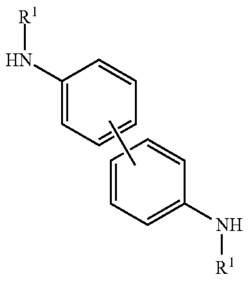

E2

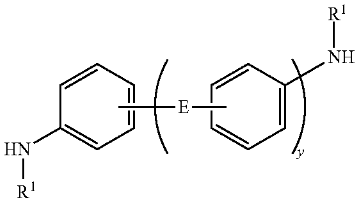

A2

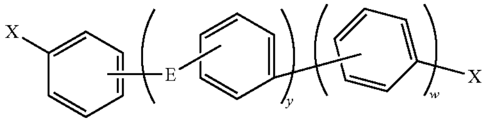

E4

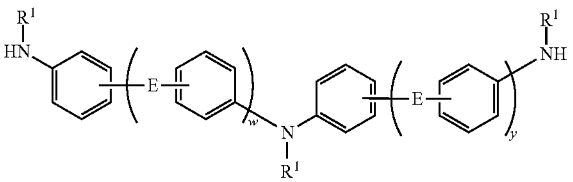

E5

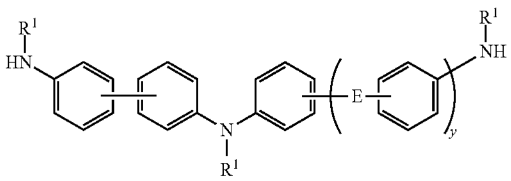

Where y is an integer equal to or greater than 1 and w is zero or an integer equal to or greater than one, and X is Cl, Br, I, boronic acid, boronic acid ester, boranes or a triflate group; and wherein X can be different at each occurrence such that carbon-carbon (for Group 1) and carbon-nitrogen bonds (for Groups 2 and 3) can be formed.

For convenience, exemplary monomers are assigned herein to Group 1, Group 2 or Group 3, and within the Groups, exemplary monomers are assigned to Subgroups such as, for example, within Group 1, subgroups A1, A2, B, C1, C2, and C3.

Homopolymers and copolymers can be made using one or more monomers from each of subgroups within each of Group 1, Group 2, and/or Group 3, provided that no copolymers containing only monomers from subgroups A or copolymers containing only monomers from subgroup B are obtained. Copolymers made from monomers within Group 3 contain at least one comonomer designated A1 or A2, and at least one comonomer from subgroup E1, E2, E3, E4 and E5. Exemplary copolymers include poly(A-co-B); poly(A-co-C); poly(A-co-B-co-C); poly(A-co-C); and copolymers comprising two or more monomers within group C, wherein, for example, "poly (A-co-B)" refers to a copolymer comprising, as polymerized units, monomers in Group A and monomers in Group B. The monomers, e.g., A and B, in such copolymers, can be present in equimolar ratios or in non-equimolar ratios. Copolymers made from monomers in Group 1 are made by formation of carbon-carbon bonds during polymerization. Copolymers made from monomers in Groups 2 and Groups 3 are made by formation of carbon-nitrogen bonds during polymerization.

The homopolymers and copolymers from Group 1 can generally be prepared using known synthetic methods. In one synthetic method, as described in Yamamoto, *Progress in Polymer Science*, Vol. 17, p 1153 (1992), the dihalo derivatives of the monomeric units are reacted with a stoichiometric amount of a zerovalent nickel compound, such as bis(1,5-cyclooctadiene)nickel(0). In another method, as described in Colon et al., *Journal of Polymer Science*, Part A, Polymer chemistry, Edition, Vol. 28, p. 367 (1990), the dihalo derivatives of the monomeric units are reacted with catalytic amounts of Ni(II) compounds in the presence of stoichiometric amounts of a material capable of reducing the divalent nickel ion to zerovalent nickel. Suitable materials include zinc, magnesium, calcium and lithium. In the third synthetic method, as described in U.S. Pat. No. 5,962,631, and published PCT application WO 00/53565, a dihalo derivative of one monomeric unit is reacted with a derivative of another monomeric unit having two reactive groups selected from boronic acid, boronic acid esters, and boranes, in the presence of a zerovalent palladium catalyst, such as tetrakis(triphenylphosphine)Pd.

Homopolymers and copolymers from Groups 2 and 3 can generally be prepared by Pd-catalyzed amination reactions. For example, homopolymers or copolymers containing monomers from Group 2 can be formed by reacting a monomer unit having both a reactive primary or secondary amine and a reactive aryl halide in the presence of copper, nickel or palladium catalysts. Homopolymers or copolymers containing monomers from Group 3 can be produced by the reaction of one or more dihalo monomeric derivative(s) with one or more diamino (primary or secondary) monomeric unit(s) in the presence of copper, nickel or palladium catalysts. Typical conditions for Pd-catalyzed amination reactions are described in Sadighi, J. P.; Singer, R. A.; Buchwald, S. L. *J. Am. Chem. Soc.* 1998, 120, 4960; Wolfe, J. P.; Tomori, H.; Sadighi, J. P.; Yin, J.; Buchwald, S. L. J., *Org. Chem.* 200, 65, 1158; Hartwig, J. F.; *Modern Arene Chemistry* 2002, 107-168, Astruc, D., Editor, Wiley-VCH Verlag GmbH & Co. KGaA, Weinheim, Germany. Typical conditions for Ni-catalyzed amination reactions are described in Desmarets, C.; Schneider, R.; Fort, Y. *Tetrahedron,* 2001, 57, 6054.; Wolfe, J. P.; Buchwald, S. L., *J. Am. Chem. Soc.* 1997, 119, 4960. Typical conditions for Cu-catalyzed amination reactions are described in Klapars, A.; Antilla, J. C.; Huang, X.; Buchwald, S. L., *J. Am. Chem. Soc.* 2001, 123, 7727.

Polymers of the compounds disclosed herein can have improved thermal stability in comparison to, e.g., NPD and TPD. For example, a compound of Formula IV wherein $R^1$ is 1-naphthyl and E is $C(CF_3)_2$ has a $T_g$ of about 240° C. Typically, the compounds have a $T_g$ of at least about 50° C., preferably at least about 100° C.

Compounds of Formulae I and IV can be prepared via carbon-nitrogen bond formation methods known to one skilled in the art. For example, homo- or hetero-polymers can be produced by the reaction of one or more dihalo monomeric derivative(s) with equimolar amounts of one or more diamino (primary or secondary) monomeric unit(s) in the presence of copper, nickel or palladium catalysts. Alternatively, one or more monomers containing an amine and a halide as reactive groups can be employed. Typical conditions for Pd-catalyzed amination reactions are described in Sadighi, J. P.; Singer, R. A.; Buchwald, S. L. *J. Am. Chem. Soc.* 1998, 120, 4960.; Wolfe, J. P.; Tomori, H.; Sadighi, J. P.; Yin, J.; Buchwald, S. L. *J. Org. Chem.* 200, 65, 1158.; Hartwig, J. F. *Modern Arene Chemistry* 2002, 107-168. Editor: Astruc, D., Wiley-VCH Verlag GmbH & Co. KGaA, Weinheim, Germany. Typical conditions for Ni-catalyzed amination reactions are described in Desmarets, C.; Schneider, R.; Fort, Y. *Tetrahedon,* 2001, 57, 6054.; Wolfe, J. P.; Buchwald, S. L. *J. Am. Chem. Soc.* 1997, 119, 4960. Typical conditions for Cu-catalyzed amination reactions are described in Klapars, A.; Antilla, J. C.; Huang, X.; Buchwald, S. L. *J. Am. Chem. Soc.* 2001, 123, 7727.

For example, a diamine monomer E1 from Group 3, such as N,N'-diphenylbenzidine, is reacted with an equimolar amount of a dihalide monomer A1, such as 4,4'-bromophenylisopropylidene, in presence of a suitable base, such as $NaO^tBu$, catalytic (less than one equivalent) amount of a suitable palladium compound, such as tris(dibenzylideneacetone) dipalladium, and a suitable ligand, such as $P(^tBu)_3$. The polymerization is conducted at a temperature between 22° C. to 150° C. for 24 to 92 hours. The resulting polymer is then treated with an endcapping group, such as bromobenzene, and allowed to further react for another 24 to 48 hours to produce a polymer of Formula IV, where $R^1$ is phenyl, E is $C(CH_3)_2$ and $R^2{=}R^3$ is phenyl.

In another example, monomer D1 from Group 2, such as 4-(N-phenylamine)-4'-(bromophenyl)isopropylidene, can be polymerized using conditions described above to give a polymer of Formula IV, where $R^1$ is phenyl, E is $C(CH_3)_2$ and $R^2{=}R^3$ is phenyl.

Compounds of Formula III can be prepared via carbon-carbon bond formation methods known to one skilled in the art. In one method, described in Yamamoto, Progress in Polymer Science, Vol. 17, p 1153 (1992), the dihalo derivatives of the monomeric units are reacted with a stoichiometric amount of a zerovalent nickel compound, such as bis(1,5-cyclooctadiene)nickel(0). In the second method, as described in Colon et al., Journal of Polymer Science, Part A, Polymer chemistry Edition, Vol. 28, p. 367 (1990), the dihalo derivatives of the monomeric units are reacted with catalytic amounts of Ni(II) compounds in the presence of stoichiometric amounts of a material capable of reducing the divalent nickel ion to zerovalent nickel. Suitable materials include zinc, magnesium, calcium and lithium. In the third synthetic method, as described in U.S. Pat. No. 5,962,631, and published PCT application WO 00/53565, a dihalo derivative of one monomeric unit is reacted with a derivative of another monomeric unit having two reactive groups selected from boronic acid, boronic acid esters, and boranes, in the presence of a zerovalent palladium catalyst, such as tetrakis(triphenylphosphine)Pd.

For example, a polymeric composition of monomer C2 from Group 1, such as 4,4'-N,N'-[(1-naphthyl)(4-chlorophenyl)]-(hexafluoroisopropylidene) is reacted with a stoichiometric amount of a zerovalent nickel compound, such as bis(1,5-cyclooctadiene)nickel(0), at a temperature between 22° C. to 150° C. for 24 to 92 hours.

For making electronic devices, including OLED devices, in one embodiment, the compounds form films when deposited onto a transparent anode such as indium-doped tin oxide (ITO). The quality of the resultant film can be superficially judged by visual/microscopic inspection for smoothness and defect density. With respect to OLEDs, it is preferred that visually observed defects be minimal. Furthermore, film quality can be measured by estimation of film thickness over several separate areas of the film using, for example, an optical ellipsometer or a mechanical profilometer; it is preferred that the films have substantially uniform thicknesses as measured in the different areas of the film.

For example, in one embodiment, compositions comprising at least one of the compounds of Formulae I, III, or IV can be in liquid form, such as a dispersion, emulsion, or solution, in making electronic devices. An exemplary process for making an electronic device, illustrated below for an organic light emitting diode, includes:

providing a liquid composition comprising a compound having a formula selected from Formula (I) and Formula (III) as described hereinabove;

providing an anode;

disposing said liquid composition comprising said compound adjacent to said anode;

removing said liquid from said composition to produce at least one hole transport layer;

providing a material selected from a photoactive material and an electrically active material;

disposing said material adjacent to said hole transport film; providing an electron transporter;

disposing said electron transporter adjacent to said emitter; and providing a cathode adjacent to said electron transporter.

In one embodiment, the liquid composition comprises at least one solvent for the compound. A suitable solvent for a particular compound or related class of compounds can be readily determined by one skilled in the art. For some applications, the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics.

Other suitable liquids mediums for use in making the liquid composition, either as a solution, emulsion, or dispersion comprising at least one of the new compounds, includes, but not limited to, chlorinated hydrocarbons (such as methylene chloride, chloroform, chlorobenzene), aromatic hydrocarbons (such as substituted and non-substituted toluenes and xylenes, including trifluorotoluene), polar solvents (such as tetrahydrofuran (THF), N-methylpyrrolidone (NMP)) esters (such as ethylacetate) alcohols (isopropanol), ketones (cyclopentanone) and mixtures thereof.

The compounds and composition comprising the compounds disclosed herein can provide the electronic advantages of smaller molecules such as triarylamines, with the solution processability, film forming capabilities, solubility properties, and thermal stability of polymeric compounds. In particular, it has been found that the compounds can be provided in solution and used in solution processes to manufacture electronic devices.

In one embodiment, the electronic devices for which the compounds are useful are OLED devices. In contrast to known compounds such as NPD (N,N'-di(naphthalen-1-yl)-N,N'-diphenyl-benzidine) and TPD (4,4'-bis[N-(3-methylphenyl)-N-phenylamino]biphenyl), which are commonly used as hole transport materials in making OLED devices, using vapor deposition processes, the present compounds have improved thermal stability and can be selectively solubilized in common solvents. By "selectively solubilized" is meant that the compounds can be made to be soluble or substantially soluble in some solvents and insoluble or substantially insoluble in other solvents. For example, in using the compounds to make electronic devices it is often desirable to provide the compound in a solvent in which the compound is soluble or substantially soluble, and deposit thereon another solvent in which the compound is insoluble or substantially insoluble. Solubilization can be provided or enhanced by variation of substituent groups on the compounds.

In one embodiment, the compound is dissolved in a solvent in which the compound is substantially soluble. The solution is then formed into a thin film and dried by any of solution processing techniques. The resultant film formed as the solvent evaporates is then further dried by baking at elevated temperatures, including above the boiling point of the solvent, either in a vacuum of nitrogen atmosphere. The film is then subjected to further processing by depositing a second solution containing emissive layer materials on top of the pre-formed compound film where the emissive materials are dissolved in a solvent in which the compound is substantially insoluble. By "substantially insoluble" is meant that less than about 5 mg of the compound dissolves in 1 ml of the solvent. However, solubilities greater than or less than 5 mg can be used and may be preferred for some applications. For example, a modest solubility up to 10 mg/mL may result in a blurred or graded interface between the HTM polymer of the present invention and the emissive layer materials. Such blurring can have deleterious or beneficial effects depending upon the natures of the materials involved. Such blurring of the interface can result in improved charge transport across the interface and substantially improved device performance or lifetime.

As will be recognized by one skilled in the art, the solubility of a compound is determined in part by substituent groups within the compound. In particular, in the compounds disclosed herein, the nature of the group "E" in the compound can be varied in order to control the solubility of a compound in a particular solvent or class of solvents. Thus, by varying the nature of the group "E", a compound can be modified such that is more or less soluble in water or any given organic non-aqueous solvent.

Also preferably, for making electronic devices, the compounds have a relatively low solubility, e.g., a solubility less than about 5 mg/mL, even about 2 mg/mL or less, in solvents that can be used to deposit an emissive layer film onto an electrode, which is typically a transparent anode such as ITO (indium doped tin oxide).

In one embodiment, there are provided electronic devices comprising at least one layer containing at least one compound or composition as disclosed herein. In one embodiment the layer is a charge transport layer and in another embodiment, the layer is a hole transport layer. The new compounds or compositions comprising such compounds can be in a separate layer, positioned between a photoactive layer and an electrode. Alternatively, a photoactive layer of an organic electronic device can contain the composition. An example of an electronic device that includes at least one layer comprising at least one compound or a composition is disclosed herein is shown in FIG. 1. The device 100 has an anode layer 110 and a cathode layer 160. Adjacent to the anode is a layer 120 comprising hole transport material. Adjacent to the cathode is a layer 140 comprising an electron transport and/or anti-quenching material. Between the hole transport layer and the electron transport and/or anti-quenching layer is the photoactive layer 130. In the illustrated embodiment, the device has an optional additional transport layer 150, next to the cathode. Layers 120, 130, 140, and 150 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary,* 470 and 476 (McGraw-Hill, Inc. 1966).

The compounds disclosed herein are particularly useful in the hole transport layer 120, and as a charge conducting host in the photoactive layer, 130. The other layers in the device can be made of any materials that are known to be useful in such layers. The anode, 110, is an electrode that is particularly efficient for injecting positive charge carriers. It can be made of, for example, materials containing a metal, mixed metal, alloy, metal oxide or mixed-metal oxide, a conducting polymer, or a combination or mixture thereof. Suitable metals include the Group 11 metals, the metals in Groups 4, 5, and 6, and the Group 8-10 transition metals. If the anode is to be light-transmitting, mixed-metal oxides of Group 12, 13 and 14 metals, such as indium-tin-oxide, are generally used. The anode 110 can also comprise an organic material such as polyaniline, as described, for example, in "Flexible light-emitting diodes made from soluble conducting polymer," *Nature* vol. 357, pp 477-479 (11 Jun. 1992). At least one of the anode and cathode is preferably at least partially transparent to allow the generated light to be observed.

The photoactive layer 130 may typically be any organic electroluminescent ("EL") material, including, but not limited to, fluorescent dyes, fluorescent and phosphorescent metal complexes, conjugated polymers, and mixtures thereof. Examples of fluorescent dyes include, but are not limited to, pyrene, perylene, rubrene, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of Iridium with phenylpyridine, phenylquinoline, or phenylpyrimidine ligands as disclosed in Petrov et al., Published PCT Application WO 02/02714, and organometallic complexes described in, for example, published applications US 2001/0019782, EP 1191612, WO 02/15645, and EP 1191614; and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1-3), 379-383, and Campbell et al., in Phys. Rev. B, Vol. 65 085210. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In one embodiment, the photoactive layer 130 comprises an organometallic compound. These electroluminescent complexes can be used alone, or doped into charge-carrying hosts, as noted above. The compounds, in addition to being useful in the hole transport layer 120, electronic transport layer 140/150 can also act as a charge carrying host for an emissive dopant in the photoactive layer 130 or otherwise part of the photoactive layer.

Examples of electron transport materials which can be used in layer 140 and/or layer 150 include metal chelated oxinoid compounds, such as tris(8-hydroxyquinolato)aluminum ($Alq_3$); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and mixtures thereof.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole transport layer 120, the electron transport layers 140 and 150, and cathode layer 160, may be surface treated to increase charge carrier transport efficiency. The choice of materials for each of the component layers is preferably determined by balancing the goals of providing a device with high device efficiency with device operational lifetime.

In one embodiment, the organic electronic device comprises at least one buffer layer between the anode 110 and the hole transport layer 120. The term "buffer layer" as used herein, is intended to mean an electrically conductive or semiconductive layer which can be used between an anode and an active organic material. A buffer layer is believed to accomplish one or more function in an organic electronic device, including, but not limited to planarization of the underlying layer, hole transport, hole injection, scavenging of impurities, such as oxygen and metal ions, among other aspects to facilitate or to improve the performance of an organic electronic device. The buffer layer can comprise at least one layer having a hole transport material, which may be a small molecule, oligomer, or polymer. Examples of hole transport materials have been summarized, for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), and porphyrinic compounds, such as copper phthalocyanine. Commonly used hole transporting polymers are polyvinylcarbazole, (phenylmethyl)polysilane, polythiophenes, and polyaniline. It is also possible to obtain hole transporting polymers by doping hole transporting molecules such as those mentioned above into polymers such as polystyrene and polycarbonate.

In one embodiment, the buffer layer comprises an electrically conducting polymer and a colloid-forming polymeric acid. As used herein, the term "colloid-forming" refers to substances that form minute particles when dispersed in aqueous solution, i.e., "colloid-forming" polymeric acids are not water-soluble. In one embodiment, the conductive polymer is selected from polythiophenes, polyanilines, and polypyrroles. In one embodiment, the colloid-forming polymeric acid is selected from polymeric sulfonic acids, polymeric phosphoric acids, polymeric phosphonic acids, polymeric carboxylic acids, polymeric acrylic acids, and mixtures thereof. In another embodiment, the colloid-forming polymeric acid is a polymeric sulfonic acid which is fluorinated. In another embodiment, the colloid-forming polymeric sulfonic acid comprises a perfluoroalkylenesulfonic acid.

In one embodiment, the buffer layer comprises poly(3,4-ethylenedioxythiophene) ("PEDT") and poly(perfluoroethylenesulfonic acid) ("PFSA"). The buffer layer can be prepared from an aqueous dispersion of PEDT/PFSA, which in turn can be prepared by the oxidative polymerization of thiophene monomers in an aqeuous dispersion of the PFSA. The preparation of PFSA is well known, and has been described in, for example, U.S. Pat. No. 6,150,426.

Examples of other organic electronic devices that may benefit from having one or more layers comprising at least one of the new compounds and compositions described herein include, but are not limited to, (1) devices that convert electrical energy into radiation (e.g., a light-emitting diode, light emitting diode display, or diode laser), (2) devices that detect signals through electronics processes (e.g., photodetectors (e.g., photoconductive cells, photoresistors, photoswitches, phototransistors, phototubes), IR detectors), (3) devices that convert radiation into electrical energy, (e.g., a photovoltaic device or solar cell), and (4) devices that include one or more electronic components that include one or more organic semi-conductor layers (e.g., a transistor or diode). Other uses for the new compositions include coating materials for memory storage devices, antistatic films, biosensors, electrochromic devices, energy storage devices, and electromagnetic shielding applications.

It is understood that each functional layer may be made up of more than one layer.

The devices can be prepared using a variety of techniques, including sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the layer(s) comprising at least one composition can be applied using solution processing techniques. Combinations of vapor deposition and solution coating of individual layers can be used. In general, the different layers will have the following range of thicknesses: anode 110, 500-5000 Å, preferably 1000-2000 Å; hole transport layer 120, 50-2000 Å, preferably 200-1000 Å; photoactive layer 130, 10-2000 Å, preferably 100-1000 Å; electron transport layer 140 and 150, 50-2000 Å, preferably 100-1000 Å; cathode 160, 200-10000 Å, preferably 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In one embodiment, an electronic device is prepared in which at least two organic layers are applied by solution processing. As used herein, the term "solution processing" is intended to mean processes that include depositing from a liquid medium. The liquid medium can be in the form of a solution, a dispersion, an emulsion, or other forms. Typical liquid deposition techniques include, but are not limited to, continuous deposition techniques such as spin coating, gravure coating, curtain coating, dip coating, slot-die coating, spray-coating, and continuous nozzle coating; and discontinuous liquid deposition techniques such as ink jet printing, gravure printing, and screen printing. In one embodiment, an electronic device is prepared in which at least two organic layers are applied by solution processing, and one of the layers applied by solution processing is a photoactive layer comprising a photoactive small molecule compound. As used herein, the term "small molecule" is intended to mean a compound having a molecular weight less than 2000. In one embodiment, the photoactive small molecule is selected from a phosphorescent organometallic compound and a fluorescent dye. In one embodiment, the photoactive small molecule is a blue luminescent material. As used here, the term "blue luminescent material" is intended to mean a material having photoluminescent and/or electroluminescent spectra with a maximum at 500 nm or less.

As used herein, the term "charge transport material" is intended to mean compounds or other compositions that can receive a charge from an electrode and facilitate its movement through the thickness of the material with relatively high efficiency and small loss of charge. Hole transport materials are capable of receiving a positive charge from an anode and transporting it. Electron transport materials are capable of receiving a negative charge from a cathode and transporting it.

The term "compound" is intended to mean a substance whose molecules consist of unlike atoms and whose constituents cannot be separated by physical means. The term "composition" is intended to be construed broadly to include mixtures, solids (in a variety of forms such as powders, flakes, pellets), or liquid formulations (wherein liquid compositions include solutions, dispersions, emulsions) and each compositions includes at least one compound described herein.

The term "anti-quenching composition" is intended to mean a material which prevents, retards, or diminishes both the transfer of energy and the transfer of an electron to or from the excited state of the photoactive layer to an adjacent layer.

The term "photoactive" refers to any material that exhibits electroluminescence, photoluminescence, and/or photosensitivity.

The term "group" is intended to mean a part of a compound, such as a substituent in an organic compound. Unless otherwise indicated, all groups can be unsubstituted or substituted. The prefix "hetero" indicates that one or more carbon atoms have been replaced with a different atom. The prefix "fluoro" is intended to mean that one or more of the hydrogen atoms attached to a carbon have been replaced with a fluorine.

The term "alkyl" is intended to mean a group derived from an aliphatic hydrocarbon having one point of attachment. The term "alkylene" is intended to mean a group derived from an aliphatic hydrocarbon and having two or more points of attachment. The term "alkenyl" is intended to mean a group derived from a hydrocarbon having one or more carbon-carbon double bonds and having one point of attachment. The term "alkynyl" is intended to mean a group derived from a hydrocarbon having one or more carbon-carbon triple bonds and having one point of attachment. The term "alkenylene" is intended to mean a group derived from a hydrocarbon having one or more carbon-carbon double bonds and having two or more points of attachment. The term "alkynylene" is intended to mean a group derived from a hydrocarbon having one or more carbon-carbon triple bonds and having two or more points of attachment.

The term "aryl" is intended to mean a group derived from an aromatic hydrocarbon having one point of attachment. The term "arylalkylene" is intended to mean a group derived from an alkyl group having an aryl substituent.

The term “arylene” is intended to mean a group derived from an aromatic hydrocarbon having two points of attachment. The term “arylenealkylene” is intended to mean a group having both aryl and alkyl groups and having one point of attachment on an aryl group and one point of attachment on an alkyl group. Unless otherwise indicated, all groups can be unsubstituted or substituted. The phrase “adjacent to,” when used to refer to layers in a device, does not necessarily mean that one layer is immediately next to another layer. On the other hand, the phrase “adjacent R groups,” is used to refer to R groups that are next to each other in a chemical formula (i.e., R groups that are on atoms joined by a bond).

The term “polymeric” or “polymer” is intended to encompass dimeric, oligomeric, homopolymeric and copolymeric species.

In addition, the IUPAC numbering system is used throughout, where the groups from the Periodic Table are numbered from left to right as 1 through 18 (CRC Handbook of Chemistry and Physics, 81st Edition, 2000).

The term “layer” or “film” refers to a coating covering a desired area. The area can be as large as an entire display, or as small as a specific function area such as a single sub-pixel. Films can be formed by any conventional deposition technique.

As used herein, the terms “comprises,” “comprising,” “includes,” “including,” “has,” “having” or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, “or” refers to an inclusive or and not to an exclusive or. For example, a condition A or B is satisfied by any one of the following: A is true (or present) and B is false (or not present), A is false (or not present) and B is true (or present), and both A and B are true (or present).

Also, “the”, “a” or “an” are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Unless otherwise defined, all letter symbols in the figures represent atoms with that atomic abbreviation. Although methods and materials similar or equivalent to those described herein can be used in the practice or testing of the present invention, suitable methods and materials are described below.

All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The following examples illustrate certain features and advantages of the present invention. They are intended to be illustrative of the invention, but not limiting. All percentages are by weight, unless otherwise indicated.

Example 1

Polymer Obtained from Monomer 1

1

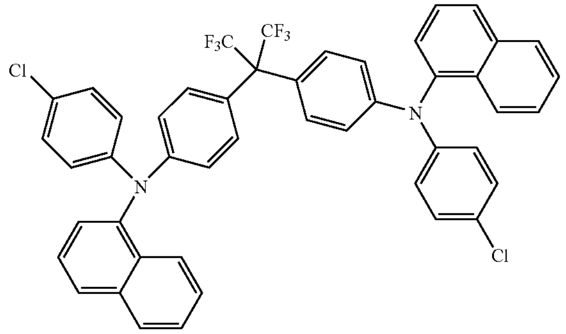

Synthesis of Monomer 1

Synthetic pathway to compound 1 is shown below.

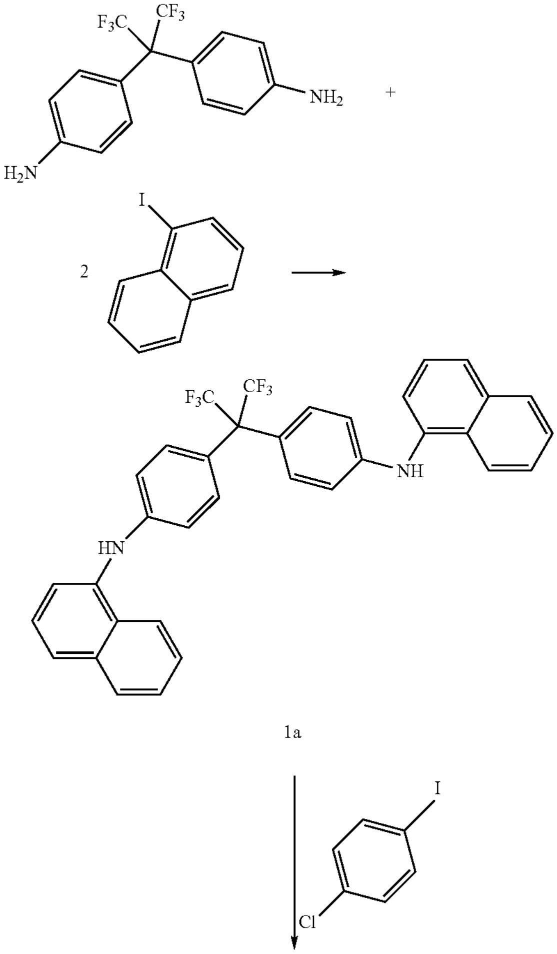

1a

-continued

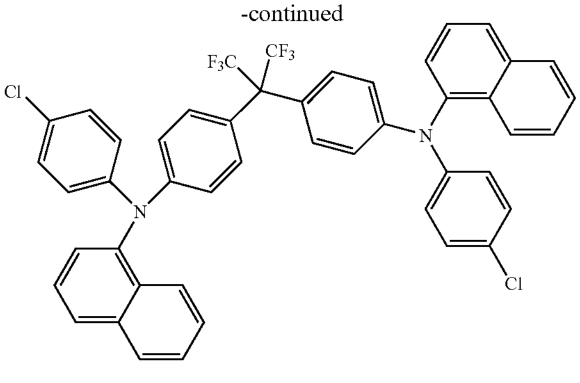

1

All reactions were performed under a nitrogen atmosphere and the reaction flask was kept away from room light. To a toluene (anhydrous, 300 mL) solution of 4,4'-(hexafluoroisopropylidene)dianiline (15.0 g), 1-iodonaphthalene (22.9 g) and NaO$^t$Bu (12.95 g), a mixture of tris(dibenzylideneacetone) dipalladium (4.12 g) and P$^t$Bu$_3$ (2.28 g) was added. The resulting reaction mixture was stirred at room temperature for five days, after which it was filtered through a plug of celite and washed with toluene (3×500 mL). The volatiles were removed by rotorary evaporation and the product was purified by column chromatography (silica) using EtOAc/hexane (1:5) followed by crystallization from $CH_2Cl_2$/hexane to yield 1a in 67% yield (17.6 g).

A toluene (anhydrous, 480 mL) solution of 1a (17.6 g) was then mixed with 1-chloro-4-iodobenzene (28.6 g), NaOtBu (8.65 g), tris(dibenzylideneacetone) dipalladium (2.20 g) and 1,1'-bis(diphenyphosphino)ferrocene (2.66 g). The resulting reaction mixture was heated to 100 C for 48 hrs, after which it was filtered through a plug of celite and washed with toluene (4×250 mL). The volatiles were removed and the product was purified by column chromatography (silica) using 1 L hexane followed by 15% $CH_2Cl_2$/hexane to give 1 as a white powder in 64% (15.4 g) yield.

Polymerization of 1

Bis(1,5-Cyclooctadiene)-nickel-(O) (3.334 g, 12.12 mmol) was added to a N,N-dimethylformamide (anhydrous, 15 mL) solution 2,2'-bipyridyl (1.893 g, 12.12 mmol) and 1,5-cyclooctadiene (1.311 g, 12.12 mmol). The resulting mixture was heated to 6° C. for 30 min. The oil bath temperature was then raised to 70 C and a toluene (anhydrous, 60 mL) solution of 1 (4.846 g, 6.0 mmol) was added rapidly to the stirring catalyst mixture. The mixture was stirred at 70 C for 92 hours. After the reaction mixture cooled to room temperature, it was poured, slowly, with vigorous stirring into 600 mL of an acetone/methanol (50:50 by volume) mixture containing ~30 mL conc. HCl. A light-gray fiberous precipitate formed which partially broke-up during stirring. The mixture was stirred for one hour and the solid was isolated by filtration. The solid was dissolved in ~200 mL of chloroform and was poured with vigorous stirring, into 1200 mL of an acetone/methanol (50:50) mixture containing ~30 mL conc. HCl. A light-gray fiberous mass formed, which was stirred for one hour and isolated by filtration. The solid was again dissolved in ~200 mL chloroform, passed through a bed (~3-4 cm) of silica gel 60. The filter bed was rinsed with ~400 mL chloroform and the combined chloroform solutions were concentrated to ~150-200 mL and poured, with vigorous stirring into 1600 mL of acetone/methanol (50:50 by volume). A slightly off-white fiberous precipitate formed, which stirred for one hour. The solid was isolated by filtration and was dried under vacuum overnight. The solid was dissolved in tetrahydrofuran (250 mL) and then slowly poured with vigorous stirring into 1500 mL of ethyl acetate. The polymer precipitated out as a slightly off-white fiberous slurry. After stirring this mixture for one hour the precipirate was isolated by filtration. This solid was re-dissolved on more time in tetrahydrofuran (220 mL), filtered through a 0.2 um syringe filter (PTFE filter membrane) and poured, slowly, with vigorous stirring into 1200 mL of methanol. The polymer precipitated out as a white fiberous slurry, which was isolated by filtration. After drying the resulting material under vacuum overnight 3.31 g (75%) of polymer was isolated. GPC (THF, room temperature): Mn=92,000; Mw=219,900; Mw/Mn=2.39.

Example 2

Synthesis of Polymer 2

Synthetic pathway to polymer 2 is shown below.

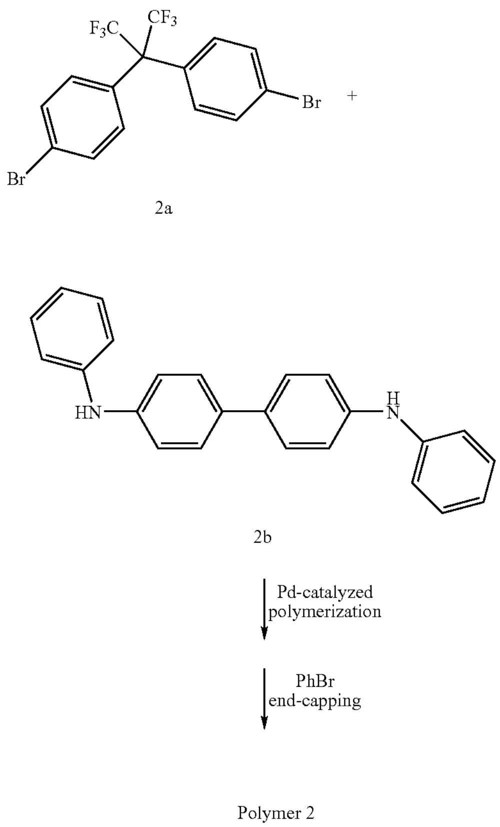

2a

2b

Polymer 2

All manipulations were performed under an atmosphere of nitrogen. A 200 mL flask was charged with 4,4'-bromophenyl (hexafluoroisopropylidene) (3.64 g, 7.87 mmol), N,N-diphenylbezidine (2.67, 7.93 mmol), NaOtBu (2.29, 23.8 mmol), toluene (anhydrous, 95 mL), and a solution (10 mL, toluene) of tris(dibenzylideneacetone) dipalladium (0.363 g, 0.4 mmol) and P$^t$Bu$_3$ (0.482 g, 2.4 mmol). The resulting reaction mixture was heated to 100° C. for 48 hrs. Bromobenzene (2.74 g, 17.4 mmol) was added to the reaction mixture and allowed to stirr for an additional 24 hours. After cooling to room temperature, the mixture was opened air and diluted with 50% toluene/DMF to make a 1% solution (~one liter) which was filtered through a one inch pad of celite. The yellow filtrate was reduced in volume to ~300 mL, after which it was slowly added to a vigorously stirring solution of 50% MeOH/acetone (~1800 mL). A precipitated formed, which was isolated by filtration and dried under vacuum to give 4.892 g (97%) of an off-white solid. This was dissolved in $CHCl_3$ to make a ~8% solution which was added dropwise to vigorously stirring 6× volume of hexanes to produce a solid. After filtering and drying, the resulting solid was dissolved in $CHCl_3$ (1% solution) and again precipitated in 6× volume of boiling acetonitrile. The precipitated was filtered and vacuum dried to yield 2.274 g of pale yellow powdery material. GPC (THF, room temperature): Mn=10,100; Mw=20,800; Mw/Mn=2.06.

Example 3

Synthesis of Polymer 3

Synthetic pathway to polymer 3 is shown below.

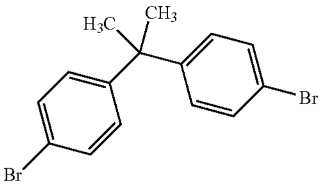

+

3a

-continued

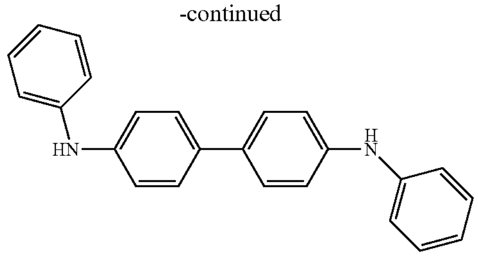

3b

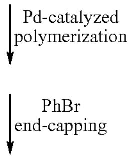

Polymer 3

All manipulations were performed under an atmosphere of nitrogen. A 200 mL flask was charged with 4,4'-bromophenylisopropylidene (1.00 g, 2.82 mmol), N,N-diphenylbezidine (0.96 g, 2.82 mmol), NaO$^t$Bu (0.85, 8.5 mmol), toluene (anhydrous, 30 mL), and a solution (5 mL, toluene) of tris (dibenzylideneacetone) dipalladium (0.13 g, 0.14 mmol) and P$^t$Bu$_3$ (0.17 g, 0.85 mmol). The resulting reaction mixture was heated to 100° C. for 48 hrs. Bromobenzene (0.98 g, 0.62 mmol) and tris(dibenzylideneacetone) dipalladium (0.032 g) and P$^t$Bu$_3$ (0.042 g). After additional 24 hrs, the reaction mixture was diluted with 50% toluene/DMF to make a 1% solution. After filtration the solvent was evaporated and the resulting solid was dissolved with $CHCl_3$ (1 L) then concentrated to a viscous solution, which was precipitated in hexanes and filtered twice to remove all particles. The powder was dried overnight and then dissolved in chloroform and re-precipitated in boiling $CH_3CN$ and filtered twice. After drying a pale-yellow powder was isolated in 42% yield (0.629 g). Mn=3370; Mw=10,200; Mw/Mn=3.02.

Example 4

Synthesis of Dimer 4

4

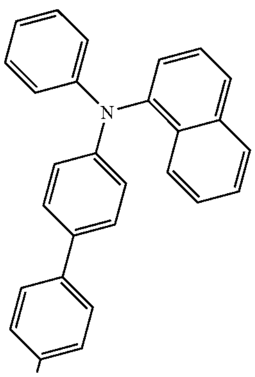

-continued

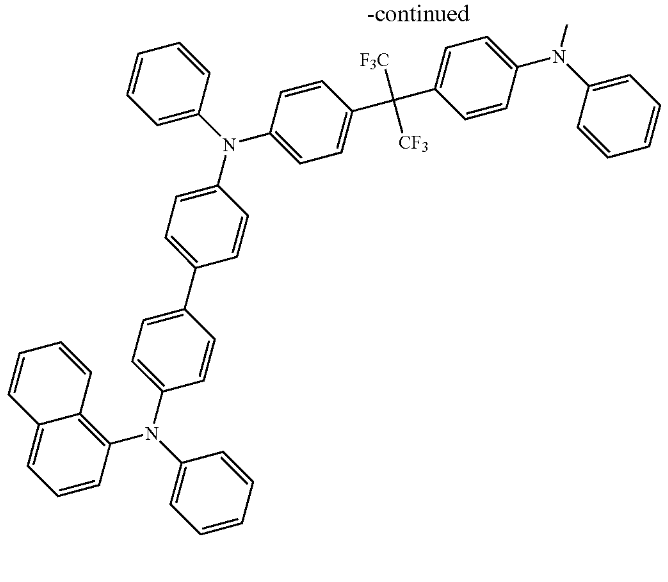

All manipulations were carried under an atmosphere of nitrogen. A Schlenk flask was charged with N,N'-diphenyl-N-naphth-1-yl-benzidine (2.00 g, 4.32 mmol), 4,4'-bromophenyl(hexafluoroisopropylidene) (0.95 g, 2.06 mmol), NaOtBu (0.623 g, 23.8 mmol), toluene (anhydrous, 40 mL), and a solution (5 mL, toluene) of tris(dibenzylideneacetone) dipalladium (0.198 g, 0.2 mmol) and $P^tBu_3$ (0.262 g, 1.3 mmol). The mixture was heated to 100 C for 12 hrs. After cooling to room temperature the solution was diluted with $CH_2Cl_2$ and filtered through celite. Evaporation of volatiles gave a brown solid that was dissolved in a minimum of $CH_2Cl_2$ and precipitate from MeOH. After filtration and drying the solid was purified by chromatography (silica, 1:2 $CH_2Cl_2$/Hexanes. Further purification by crystallization ($CH_2Cl_2$/MeOH) yielded compound 4 as an off-white powder in 81% yield (2.04 g). $^1$H NMR ($CD_2Cl_2$, 500 MHz): δ 7.97 (d, 2H); 7.92 (d, 2H); 7.82 (d, 2H); 7.49 (m, 8H); 7.40 (m, 8H); 7.30 (t, 4H); 7.24 (m, 8H); 7.15 (m, 8H); 7.06 (m, 8H); 6.97 (t, 2H); $^{19}$F NMR ($CD_2Cl_2$, 376.86 MHz): δ-64.66 (s).

Example 5

Synthesis of Dimer 5

5

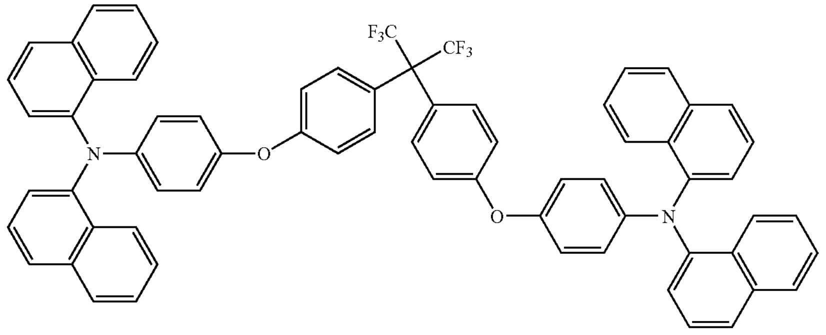

All manipulations were carried under an atmosphere of nitrogen. A round bottom flask 4",4'"-(hexafluoroisopropylidene)bix(4-phenoxyaniline) (10.08 g, 19.5 mmol), 1-iodonaphthalene (14.83 g, 58.4 mmol), NaOtBu (5.61 g, 58.4 mmol), toluene (anhydrous, 300 mL), and a solution (10 mL, toluene) of tris(dibenzylideneacetone) dipalladium (1.78 g, 1.95 mmol) and $P^tBu_3$ (0.98 g, 4.87 mmol). The mixture was stirred at room temperature for four days. The resulting mixture was washed with water, and the organic layer was dried over $MgSO_4$. Removal of volatiles yielded a brown oil which was purified by column chromatography using hexane (1.5 L) followed by hexane:EtOAc mixture of increasing polarity up to pure EtOAc. The desired compound 5 was isolated as a white powder (1.0 g). $^1$H NMR ($CD_2Cl_2$, 500 MHz): δ 8.03 (d, 1H); 7.85 (d, 1H); 7.67 (d, 1H); 7.43 (t, 1H); 7.30 (m, 3H); 7.17 (d, 1H); 6.88 (d, 1H); 6.83 (d, 1H); 6.72 (d, 1H); $^{19}$F NMR ($CD_2Cl_2$, 376.86 MHz): δ-64.81 (s).

Example 6

In this example, a second sample of polymer 1 was synthesized.

Bis(1,5-Cyclooctadiene)-nickel-(O) (22.01 g, 80 mmol) was added to a N,N-dimethylformamide (anhydrous, 100 mL) solution 2,2'-bipyridyl (8.65 g, 80 mmol) and 1,5-cyclooctadiene (1.311 g, 12.12 mmol). The resulting mixture was heated to 6° C. for 30 min. The oil bath temperature was then raised to 70 C and a toluene (anhydrous, 400 mL) solution of monomer 1 from Example 1 (30.7 g, 38 mmol) was added rapidly to the stirring catalyst mixture. The mixture was stirred at 70 C for 5 days. After the reaction mixture cooled to room temperature, it was poured, slowly, with vigorous stirring into-100 mL conc. HCl. The resulting mixture was stirred for an hour and then added to 6 L of an acetone/methanol (50:50 by volume) mixture containing ~100 mL conc. HCl. A light-gray fiberous precipitate formed which partially broke-up during stirring. The mixture was stirred for 1.5 hours and the solid was isolated by filtration. The solid was dissolved in ~1200 mL of chloroform and filtered through a plug of silica. The resulting solution was poured with vigorous stirring, into 6.4 L of an acetone/methanol (50:50) mixture containing ~320 mL conc. HCl. A light-gray fiberous mass formed, which was stirred for one hour and isolated by filtration. The solid was again dissolved in ~1500 mL chloroform and precipitated as described above. The solid was isolated by filtration and was dried under vacuum overnight. The solid was dissolved in chloroform (1200 mL) and then slowly poured with vigorous stirring into 3 L of ethyl acetate. The polymer precipitated out as a white fiberous slurry, which was isolated by filtration. After drying the resulting material under vacuum overnight 25.0 g (88%) of polymer was isolated. GPC (THF, room temperature): Mn=43,700; Mw=119,200; Mw/Mn=2.73.

Example 7

In this example an OLED is made by solution processing of the organic layers, with a new polymer as the hole transport layer.

a. TCTA

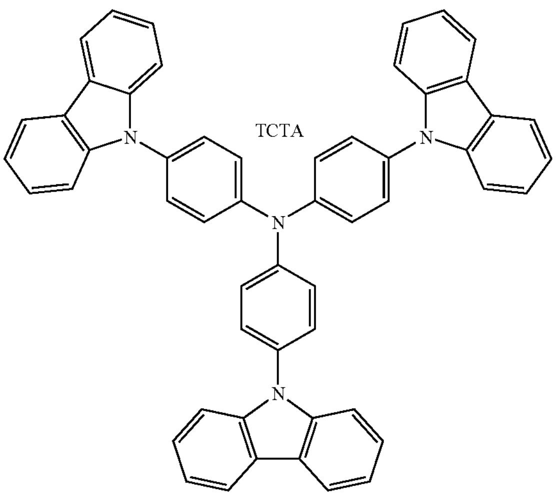

TCTA

TCTA is available commercially from HW Sands (Jupiter, Fla.). It can be made as follows. In a dry box a 2-L round-bottomed flask was charged with tri(p-bromophenyl)amine, carbazole, Pd catalyst tris(dibenzylideneacetone) dipalladium, di(t-butyl)o-biphenylphosphine, and toluene. To this stirring mixture, Na butoxide was added. A condenser and septum were attached and the flask brought out of the dry box. The mixture was refluxed for 14 hours under nitrogen before being diluted with ether and the combined organic layers dried over magnesium sulfate and concentrated to dryness affording a brown solid. The solid was dissolved in hot toluene and precipitated out with the addition of hexanes. The filtrate was a tan solid. This solid was dissolved in hot toluene and silica gel was added to the stirring mixture. The stirring mixture was filtered and concentrated until precipitate was visible. Hexanes were added to drive the precipitation, resulting in 14 g of a tan fluffy solid. This sold was dissolved in 40 mL dichloromethane ("DCM") and hexanes (2:1) and stirred until the volume was reduced to ⅓. This mixture was filtered affording a tan powder. This was further purified by flash chromatography over silica using DCM:Hexane (2:1)->DCM. Some fractions appeared pure by HPLC but were colored yellow. These fractions were discarded and only colorless fractions pure by HPLC were kept. Final yield of the first crop was 5.2 g (15%).

b. PEDOT/PFSA

This was made according to the procedure in co-pending application Ser. No. 10/669,494, filed Sep. 24, 2003. The Nafion® was a 12.5% (w/w) aqueous colloidal dispersion with an EW of 990. A 25% (w/w) dispersion was made using a procedure similar to the procedure in U.S. Pat. No. 6,150,426, Example 1, Part 2, except that the temperature is approximately 270° C. This was diluted to form the 12.5% (w/w) dispersion.

In a 2000 mL reaction kettle are put 715 g of 12% solid content aqueous Nafion® (82 mmol $SO_3H$ groups) dispersion, 1530 g water, 0.5 g (0.98 mmol) iron(III) sulfate ($Fe_2(SO_4)_3$), and 1011 μL of concentrated $H_2SO_4$ (18.1 mmol). The reaction mixture is stirred for 15 min at 276 RPM using an overhead stirrer fitted with a double stage propeller type blade, before addition of 8.84 g (37.1 mmol) sodium persulfate ($Na_2S_2O_8$) in 60 mL of water, and 3.17 mL ethylenedioxythiophene ("EDT", from H. C. Starck, GmbH) is started from separate syringes using addition rate of 4.2 mL/h for $Na_2S_2O_8$/water and 224 μL/h for EDT while continuously stirring at 276 RPM. The addition of EDT is accomplished by placing the monomer in a syringe connected to a Teflon® tube that leads directly into the reaction mixture. The end of the Teflon® tube connecting the $Na_2S_2O_8$/water solution was placed above the reaction mixture such that the injection involved individual drops falling from the end of the tube. The reaction is stopped 7 hours after the addition of monomer has finished by adding 170 g each of Lewatit MP62WS, a weakly basic anion exchange resin (from Bayer, Pittsburgh, Pa.) and Lewatit® MonoPlus S100, a strongly acidic, sodium cation exchange resin (from Bayer, Pittsburgh, Pa.), and 225 g of n-propanol to the reaction mixture and stirring it further for 7 hours at 130 RPM. The ion-exchange resin is finally filtered from the dispersion using Whatman No. 54 filter paper. The pH of the dispersion is ~4 and dried films derived from the dispersion have a conductivity of $2.6\times10^{-5}$ S/cm at room temperature.

c. TPBI 2,2',2"-(1,3,5-phenylene)-tris[1-phenyl-1 h-benzimidazole] ("TPBI") can be made according to the procedure in U.S. Pat. No. 5,645,948.

d. Device Fabrication

Patterned ITO substrates were cleaned with UV ozone for 10 minutes. Immediately after cooling, the aqueous dispersion of PEDT/Nafion® made above was spin-coated over the ITO surface to form a buffer layer. The cathode leads were wiped clean with damp swabs and the substrates were then baked in vacuo at 90° C. for 30 minutes. After cooling, the substrates were then spin-coated with a 1% w/v solution of Polymer 1, from Example 6, in toluene and then baked again at 130° C. for 30 minutes. After cooling the substrates were spin-coated with a 1% w/v solution of 1,3,6,8-tetraphenylpyrene-TCTA (purchased from Pfaltz & Bauer, Waterbury, Conn.) in chloroform (10:90). The cathode contacts were then wiped clean with toluene wetted swabs. The substrates were masked and placed in a vacuum chamber. After pumping to a base pressure of $2\times10^{-7}$ torr, a layer of TPBI was deposited by thermal evaporation to form the electron transport layer. This was followed by a layer of LiF and then Al, to form the cathode. The chamber was then vented to nitrogen, the masks were changed and the chamber evacuated again. After reaching a base pressure of $1\times10^{-6}$ torr, a second layer of Al was deposited by thermal evaporation. The chamber was vented to nitrogen and the devices were encapsulated using a glass lid and UV curable epoxy. These devices were then tested, demonstrating electroluminescence with efficiencies of 0.6 cd/A at 6 V, and blue light with cie coordinates of x=0.165, y=0.102.

What is claimed is:

1. A compound having Formula (III):

(III)

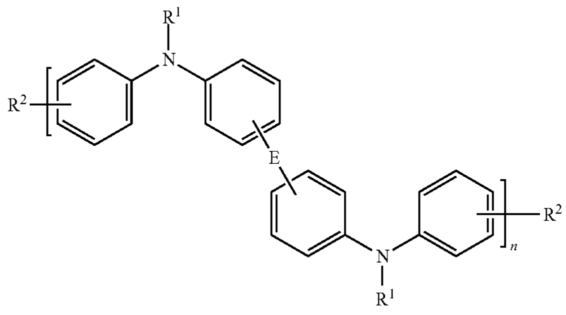

wherein:

n is an integer of at least 1;

$R^1$ is aryl;

$R^2$ is selected from Cl, Br, and I $R^5$ and $R^6$ are fluoroalkyl; and

E is $(CR^5R^6)_m$ wherein m is 1.

2. A composition comprising at least one compound having the Formula of claim 1.

3. The composition of claim 2 wherein said composition is a liquid composition.

4. A device comprising at least one layer comprising at least one compound having Formula (III):

(III)

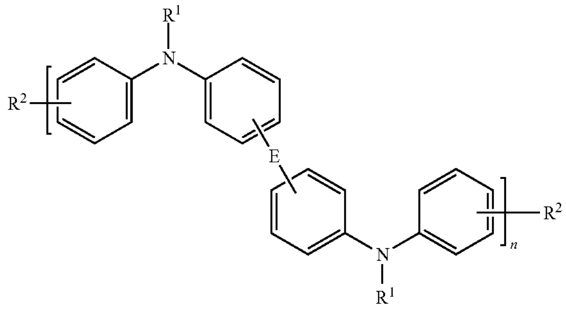

-continued (III)

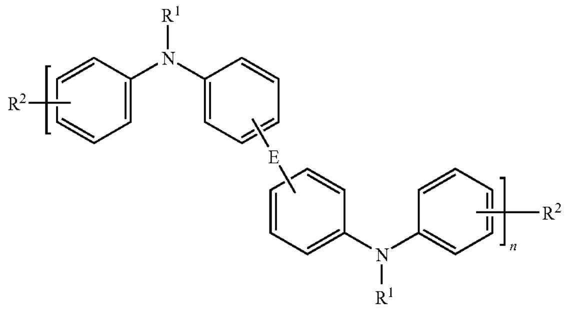

wherein:

n is an integer of at least 1;

$R^1$ is aryl;

$R^2$ is selected from Cl, Br, and I $R^5$ and $R^6$ are fluoroalkyl; and

E is $(CR^5R^6)_m$ wherein m 1, said device is selected from devices that convert electrical energy into radiation, devices that detect signals through electronics processes, that convert radiation into electrical energy, devices having at least one electronic component, memory storage devices, energy storage devices, antistatic films, biosensor devices, electrochromic devices, and electromagnetic shielding applications.

5. A device according to claim 4, wherein the layer comprising a compound having Formula (III) is a hole transport layer.

6. A polymer made from the compound of claim 1.

7. A device having at least one layer comprising the polymer of claim 6.

* * * * *